(12) United States Patent
Psaltis et al.

(10) Patent No.: US 7,367,505 B2
(45) Date of Patent: May 6, 2008

(54) METHOD AND A SYSTEM TO DISPENSE AND DETECT FLUORESCENT QUANTUM DOTS

(75) Inventors: Demetri Psaltis, Pasadena, CA (US); Christophe Moser, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 418 days.

(21) Appl. No.: 10/865,077

(22) Filed: Jun. 9, 2004

(65) Prior Publication Data

US 2005/0017079 A1    Jan. 27, 2005

Related U.S. Application Data (60) Provisional application No. 60/477,911, filed on Jun. 12, 2003.

(51) Int. Cl.
*G06K 7/10*    (2006.01)

(52) U.S. Cl. .................. 235/454; 235/435; 235/439; 235/494

(58) Field of Classification Search .............. 235/454, 235/468, 435, 439, 494; 369/108
See application file for complete search history.

(56) References Cited

U.S. PATENT DOCUMENTS

| | | | |
|---|---|---|---|
| 6,633,370 B2 * | 10/2003 | Lawandy | 356/71 |
| 7,121,474 B2 * | 10/2006 | Bourianoff et al. | 235/494 |
| 7,124,441 B1 * | 10/2006 | Gaston | 726/26 |

\* cited by examiner

*Primary Examiner*—Seung Ho Lee
(74) *Attorney, Agent, or Firm*—J. D. Harriman, II; DLA Piper US LLP (57) ABSTRACT

The invention combines fluorescent QDs and methods to dispense and detect them efficiently in a compact volume for a range of optical tagging applications. Micro-fluidic devices are used for mixing water-soluble fluorescent QDs in aqueous solutions to create a multi color fluorescent nano-optical tag, and gratings are used for spreading the spectral components of the fluorescent signal leading to an improvement in optical data storage capacity over prior art methods. The spectral signature of the tag is detected by a compact read-out head with a grating spectrometer. One way is to dispense the tag within the pits of a DVD or CD using an ink-jet nozzle and exciting them by a large range of wavelengths each shorter that the emission peak. The filters have a high immunity to prolonged exposure to high temperatures, and up to 41 infrared filters can be holographically recorded by spatial multiplexing of the substrate.

29 Claims, 12 Drawing Sheets

METHOD AND A SYSTEM TO DISPENSE AND DETECT FLUORESCENT QUANTUM DOTS

CROSS-REFERENCE TO RELATED APPLICATIONS

The present application claims the benefit of priority from pending U.S. Provisional Patent Application No. 60/477,911, entitled "Optical Tags: Devices and Applications", filed on Jun. 12, 2003, which is herein incorporated by reference in its entirety.

BACKGROUND OF THE INVENTION

1. Field of the Invention

The present invention relates to the field of image sensing devices and applications. More specifically, the present invention relates to a technology that combines fluorescent nano-particles (quantum dots) and methods to dispense and detect them for a range of optical tagging applications.

Portions of the disclosure of this patent document contain material that is subject to copyright protection. The copyright owner has no objection to the facsimile reproduction by anyone of the patent document or the patent disclosure as it appears in the Patent and Trademark Office file or records, but otherwise reserves all rights whatsoever.

2. Background Art

An increase in the awareness for security and fraud protection systems at many levels has created an influx in tagging applications in such fields as security/identification, counterfeit, ultra-high density data storage, manufacturing assembly, military, and civil remote sensing. Prior art tagging technologies are based on either bar-coding or radio frequency (RF). Technologies based on both bar-coding and RF have difficulties. Bar-code tags have to be manually scanned one at a time, and RF tags are at times difficult to introduce due to such handicaps as high volume/low cost, high tagging throughput of small parts, large number of combinations, and use with optical discs such as CDs and DVDs causing interference with the laser. This difficulty can be better understood with a review of prior art radio frequency identification (RDIF).

RDIF

RDIF is a means of identifying a person or an object using a radio frequency transmission, typically at 125 kHz, 13.56 MHz, or 800-900 MHz. RDIF has extensively been used in applications such as toll collection, access control, ticketing, and car immobilization devices. In recent years the technology has received an increased attention due to heightened security concerns and supply chain automation. Even though the primary benefit of RDIF tags over barcodes is their ease of use and reliability, RDIF tags cannot be placed on nano size objects or when a very high information density is required. PharmaSeq, Inc. and TAGSYS are two of the leading companies that use RDIF technology, but they both utilize circuits (about 0.25 mm) with radio frequency for applications mainly in the textile retail industry.

Figure 1:
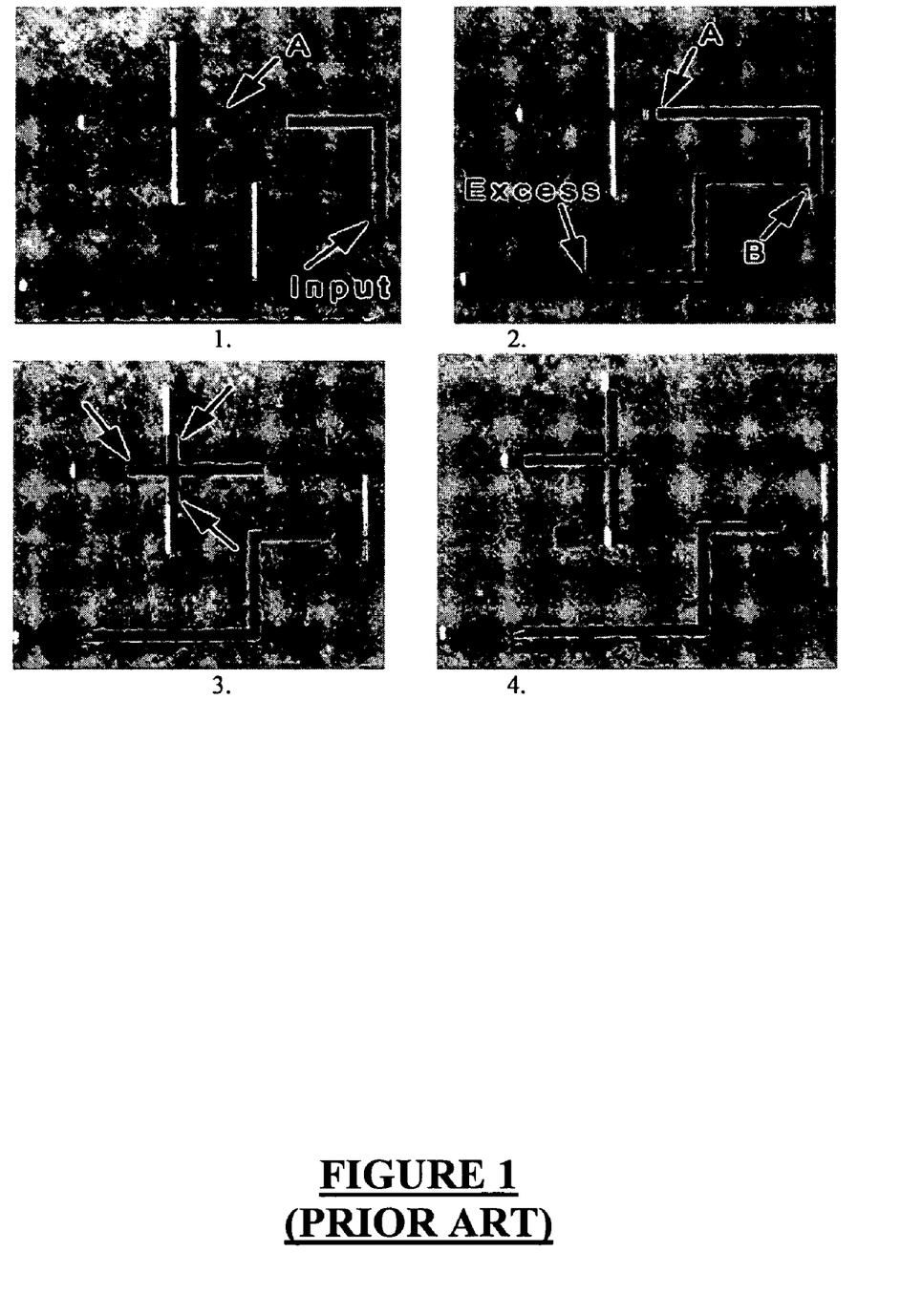
FIG. 1 illustrates a prior art chip.

There is a need for an inexpensive alternative to barcode tags and for a nano sized alternative to RDIF tags. This alternative is a micro-fluidic device that controls small quantities of fluids by creating the equivalent of a vast network of large pumping circuitry with valves, combiners, splitters, and pumps onto an integrated chip. The components of the chip can be constructed from a multitude of different polymeric platforms that enable hydrodynamic control of fluid movement. FIG. 1 illustrates one such chip that incorporates micro-valves, pumps, and splitters that partitions a sample of fluid into three equal components for further analysis. The Figure has 4 separate blocks marked 1 through 4, which will be explained further below. The liquid sample is introduced with a syringe pump and fills the measuring channel until it reaches stopping valve A (block 1). The excess fluid is diverted through valve B (block 2). The fluid sample then proceeds through valve A and begins filling the dividing channels (block 3). Finally, block 4 shows three precisely measured, equal samples ready for further analysis.

Figure 2:
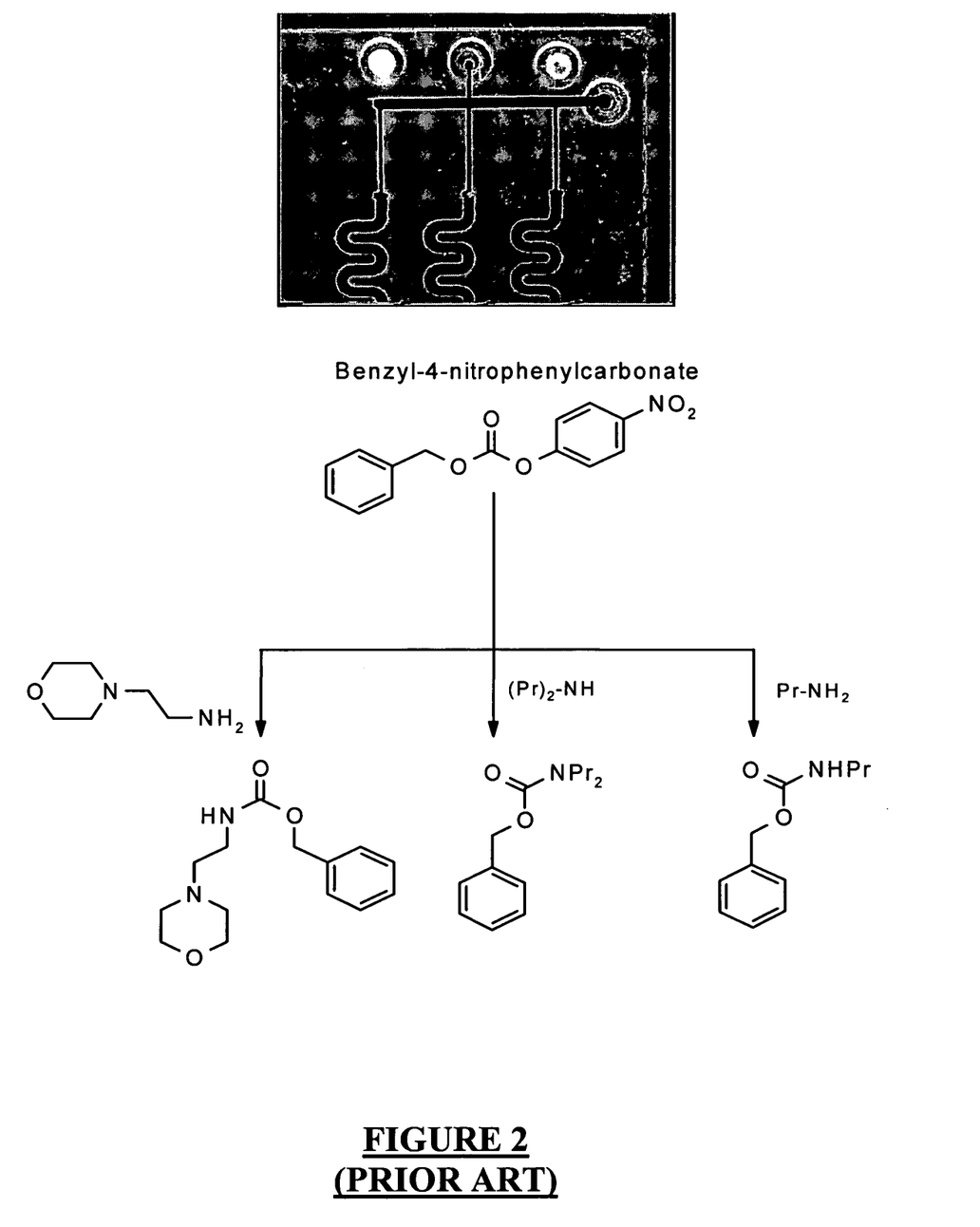
FIG. 2 illustrates another prior art chip.

FIG. 2 illustrates another prior art chip with an integrated mixer for three liquids. The flow of each channel is individually set to control the mixing ratio and perform simultaneous organic reactions in controlled ratios. In the Figure nitrophenylcarbonate is introduced in the chip at A. Three amines coming from the top of the chip at B, C, and D meet the nitrophenylcarbonate at microfluidic mixing junctions E, F, and G respectively. The mixtures are collected at exit ports (not shown) and confirmed using MS analysis. The Figure also shows, to the right, the chemical reaction between the nitrophenylcarbonate and the three amines. Certain fundamental properties of fluorescent liquid on a nano scale will better help in fully appreciating the present invention.

Fluorescent Liquid

Nanoliters volume of a liquid behaves very differently from liters volume of the same liquid. The effect of the guiding channels' walls become important at the nano scale because the walls tend to drag the liquid so that the center flows more rapidly than the edge. This characteristic could create a problem when different liquids are mixed to produce a homogeneous solution, especially organic liquids that tend to be sticky. However, chips made by several companies in the field overcomes this problem successfully.

Figure 3:
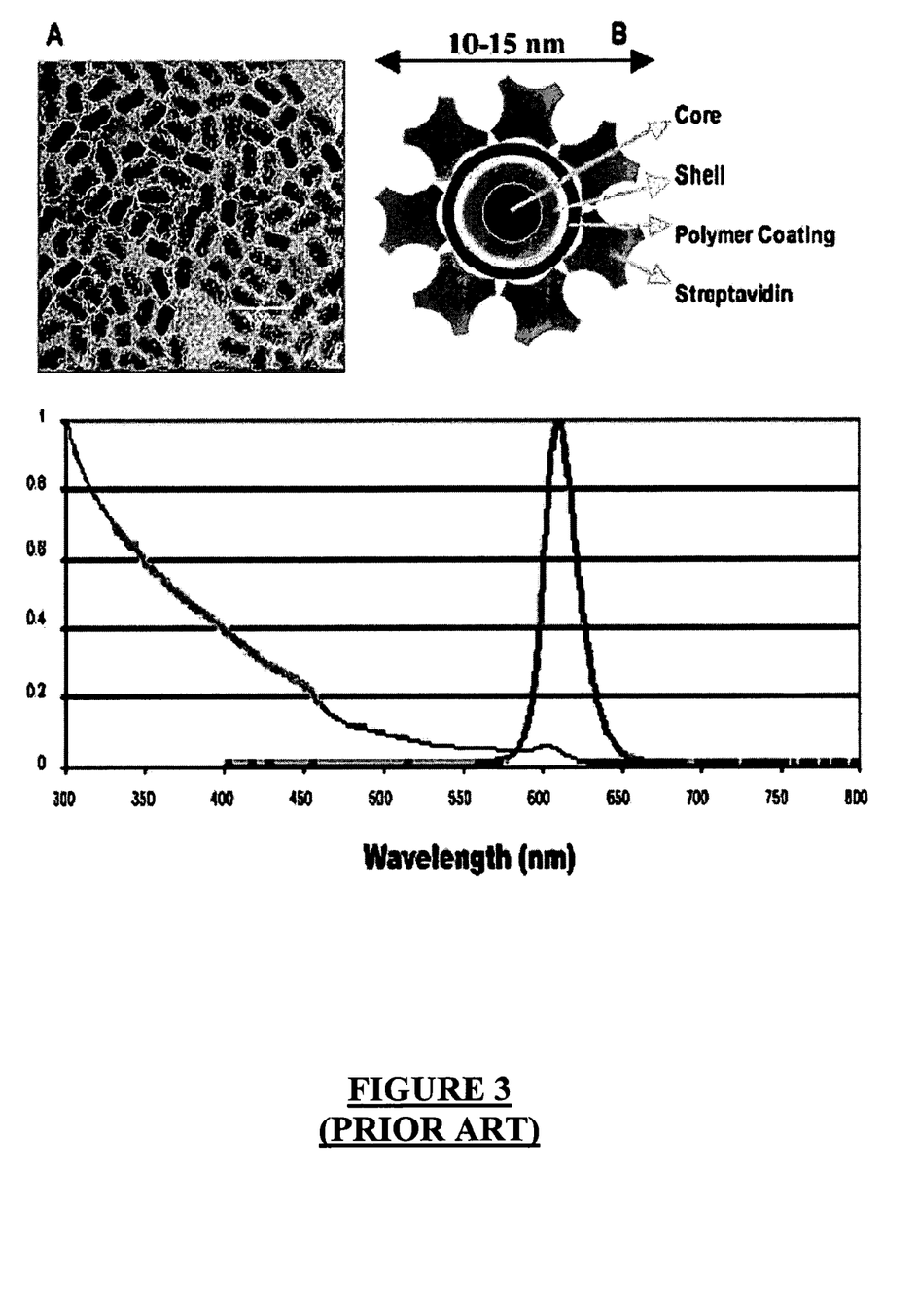
FIG. 3 illustrates an electron microscope image of a QD and its absorbance and emission graph.

For example, a homogenous solution created by mixing 39 different fluorescent quantum dots (QDs) each with 6 gray levels in a sub-micrometer spot size yields $10^{30}$ combinations (~1000 bits/$\mu m^2$). These QDs typically hold a few thousand atoms and are a few nanometers in diameter that selectively hold and release atoms. Since these QDs are composed of simple inorganic compounds making them chemically inert, and those with outer shells are stable to photochemical damage. Also, since the emission wavelength of a QD depends on its size, it is possible to tune the emission wavelength by controlling its size. The spectral linewidth may be as little as 12 nm at Full-Width Half-Maximum (FWHM) for a single nanocrystal. FIG. 3 illustrates an electron microscope image of a QD on the top. As seen in FIG. 3, the QD is about 10-15 nm across and consist of an inner core section 300 enclosed in a shell 310 which is covered in a polymer coating 320. The outermost layer is a streptavidin layer 330. The bottom of FIG. 3 illustrates a graph showing the typical absorbance and emission spectra of a typical QD with center wavelength 605 nm.

SUMMARY OF THE INVENTION

The present invention combines fluorescent nano-particles (also known as quantum dots or QDs) and methods to dispense and detect them efficiently in a compact volume for a range of optical tagging applications ranging from security/identification, counterfeit, ultra-high density data storage, manufacturing assembly, military to civil remote sensing. According to one embodiment, micro-fluidic devices are used for mixing water-soluble fluorescent nano-particles in aqueous solutions to create a multi color fluorescent tag called a nano-optical tag. According to another embodiment, gratings are used for spreading the spectral components of the fluorescent signal leading to an improvement in optical data storage capacity over prior art methods. According to another embodiment, the spectral signature of the nano-tag dispensed on the surface of the information carrying medium is detected by a compact read-out head with a grating spectrometer. According to another embodiment, the nano-tag is dispensed within the pits of a commercially available DVD or CD using an ink-jet nozzle. According to another embodiment, the QDs can be excited by a large range of wavelengths, each shorter that the emission peak. According to another embodiment, the grating spectrometer is holographic, volume, or surface. According to another embodiment, the grating filters have a high immunity to prolonged exposure to high temperatures. According to another embodiment, up to 41 infrared filters can be holographically recorded by spatial multiplexing of the substrate.

DETAILED DESCRIPTION OF THE INVENTION

The present invention relates to a technology that combines fluorescent QDs and methods to dispense and detect them for a range of optical tagging applications. In the following description, numerous specific details are set forth to provide a more thorough description of embodiments of the invention. It is apparent, however, to one skilled in the art, that the invention may be practiced without these specific details. In other instances, well known features have not been described in detail so as not to obscure the invention.

Basic Schematic

Figure 4:
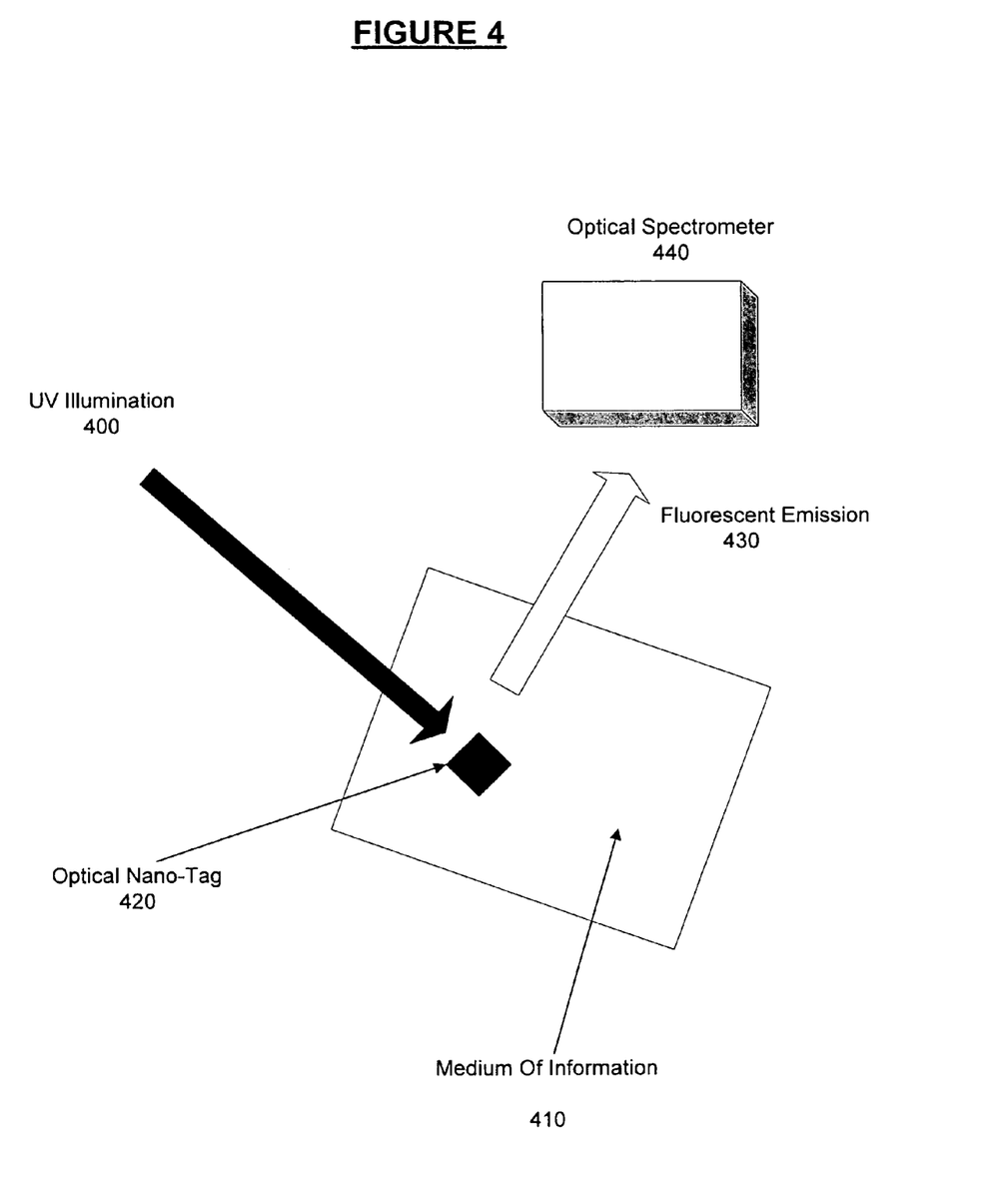
FIG. 4 illustrates the basic schematic of the present invention.

The basic schematic of the present technology is shown in FIG. 4. Optical tag 420 composed of many fluorescent QDs is disposed on the surface of medium 410 that needs protection. When UV illumination 400 is turned on, the optical tag 420 fluoresces. Optical spectrometer 440 analyzes the fluorescent emission 430 representing the passive fingerprint of the tag. According to one embodiment, medium 410 is made up of an embossed material. The embossed material has regions of pits (holes or depressions) and lands (raised portions).

Quantum Dots

Figure 5:
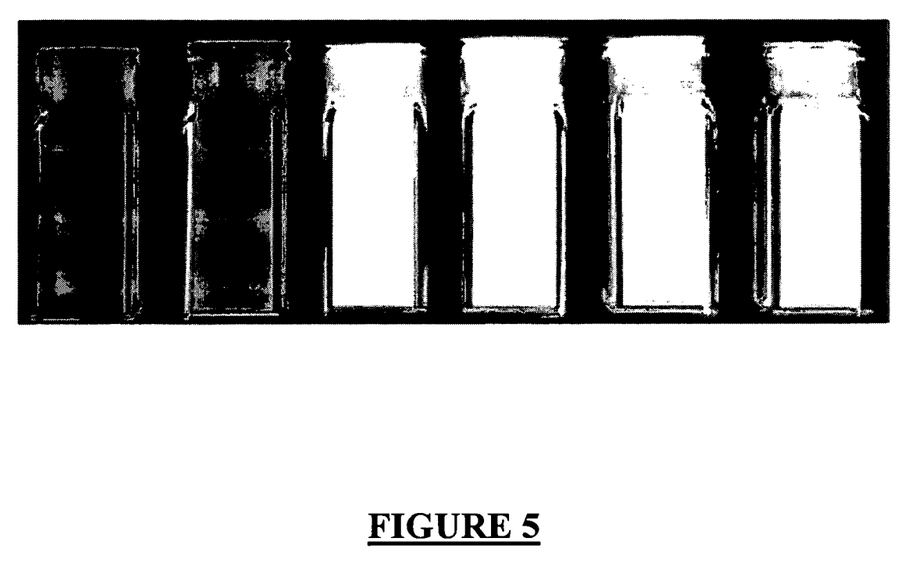
FIG. 5 illustrates the fluorescence of 6 different QDs excited with the same ultra-violet source, according to one embodiment of the present invention.

Quantum dots or QDs are nanometer-scale boxes that selectively hold or release atoms. According to one embodiment, the QDs are excited by a large range of wavelengths shorter than the emission peak. According to another embodiment, the QDs are intensely fluorescing due to the high excitation cross-section and high quantum yield. FIG. 5 illustrates the fluorescence of 6 different QDs excited with the same ultra-violet source.

Optical Spectrometer

Figure 6:
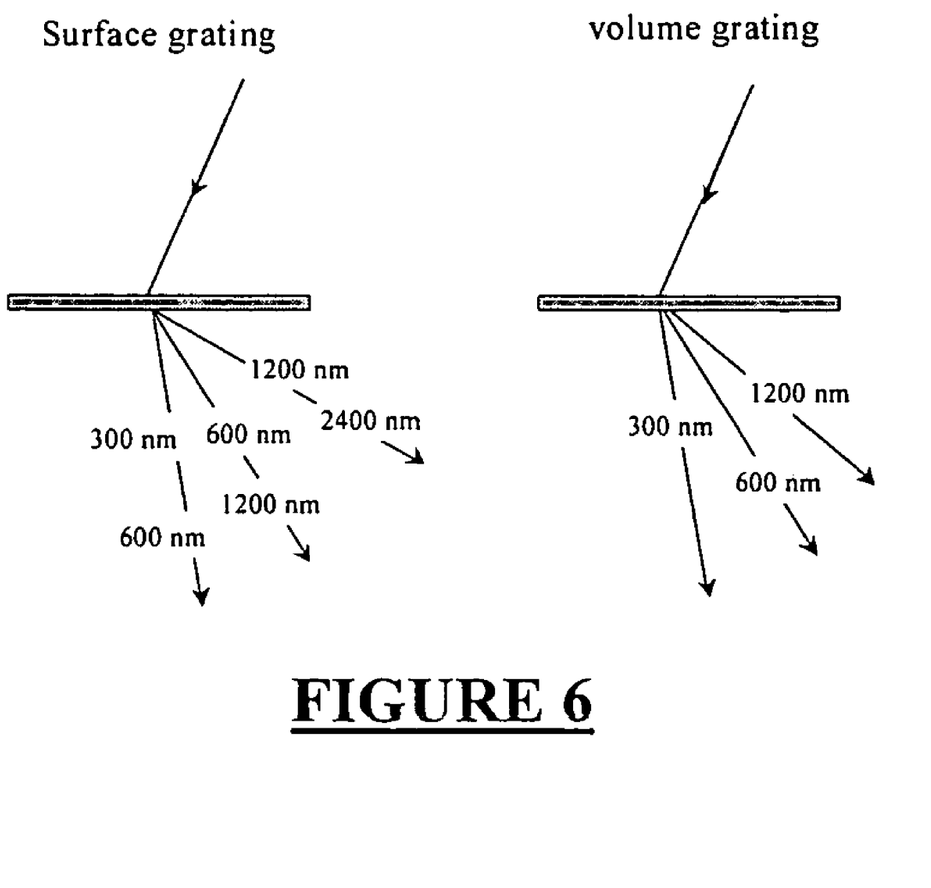
FIG. 6 illustrates the difference between a surface grating (left side of the Figure) and a volume grating (right side of the Figure).

The fluorescence of an ensemble of QDs can be analyzed by an optical spectrometer. The spectral range of QDs covers from visible (450 nm) to infrared (1500 nm). Since this range is too large to be handled by a single diffraction grating because of the overlap of the diffraction orders, and since the size of the grating-based spectrometer is several cubic centimeters, which is too bulky for the targeted applications involving optical disks, the present invention uses a volume grating spectrometer. FIG. 6 illustrates the difference between a surface grating (left side of the Figure) and a volume grating (right side of the Figure). The left side of the Figure, which is the surface grating, shows for example, the same diffraction angle for both 300 nm and 600 nm wavelengths. In contrast, the right side of the Figure, which is the volume grating, has a separate diffraction angle for each wavelength. According to another embodiment, a spectrometer based on volume gratings is chosen because it alleviates both the above mentioned disadvantages by providing a single order diffraction, large spectral range, and compact size.

The number of different QDs with different center wavelengths over a spectral range of 1050 nm is around 50, and the multiplexing of these 50 gratings in the same volume with a good spectral efficiency (>70%) is possible using the methods and holographic glass materials of the present invention (explained in further detail below).

Volume Grating Filter

Figure 7:
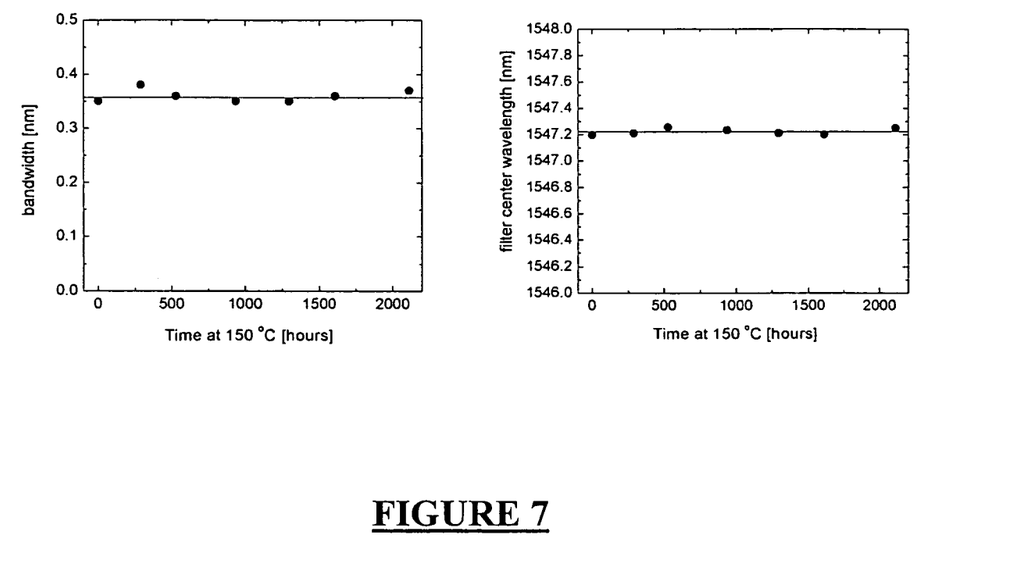
FIG. 7 illustrates a characteristic of a volume grating filter.

According to one embodiment, the volume grating filters have an extreme immunity to prolonged exposure to high temperatures. FIG. 7 illustrates the stability of a bandwidth (left side of FIG. 7) and a central filter frequency (right side of FIG. 7) of a volume grating filter exposed to a temperature of 150° C. for about 2000 hours. As can be seen from FIG. 7, the filter has an excellent robustness to temperature, and the filters show no degradation after more than 2000 hours at 150° C.

Holographic Glass Material

Figure 8:
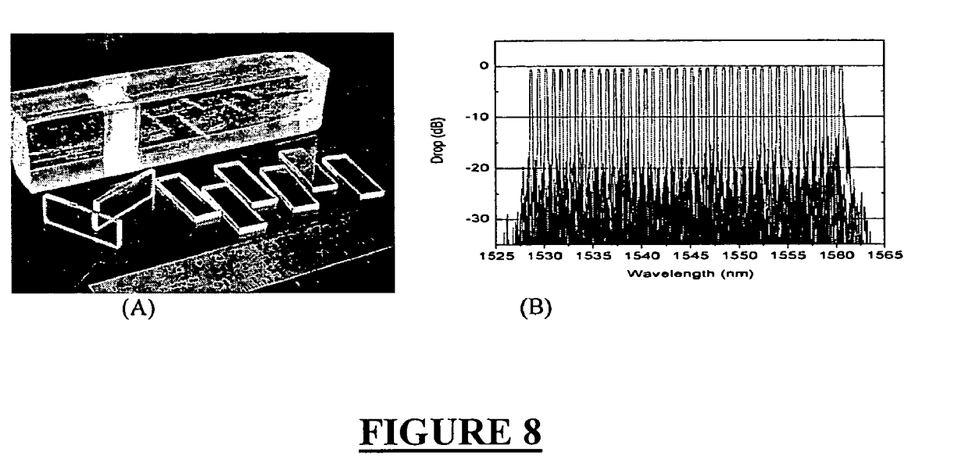
FIG. 8(A) illustrates 41 holographic glass substrates.
FIG. 8(B) illustrates filter responses of the 41 substrates of FIG. 8(A).

According to one embodiment, up to 41 infrared filters can be holographically recorded by spatial multiplexing (one filter per location) of the substrate. FIG. 8(A) illustrates these 41 holographic glass substrates and FIG. 8(B) illustrates a graph of the filter responses of the 41 substrates. The graph of FIG. 8(B) was obtained by making the bandwidth of the filters extremely narrow for telecom purposes. But, the substrates can be fabricated with broader bands as shown below.

QDs for CDs and DVDs

Figure 9:
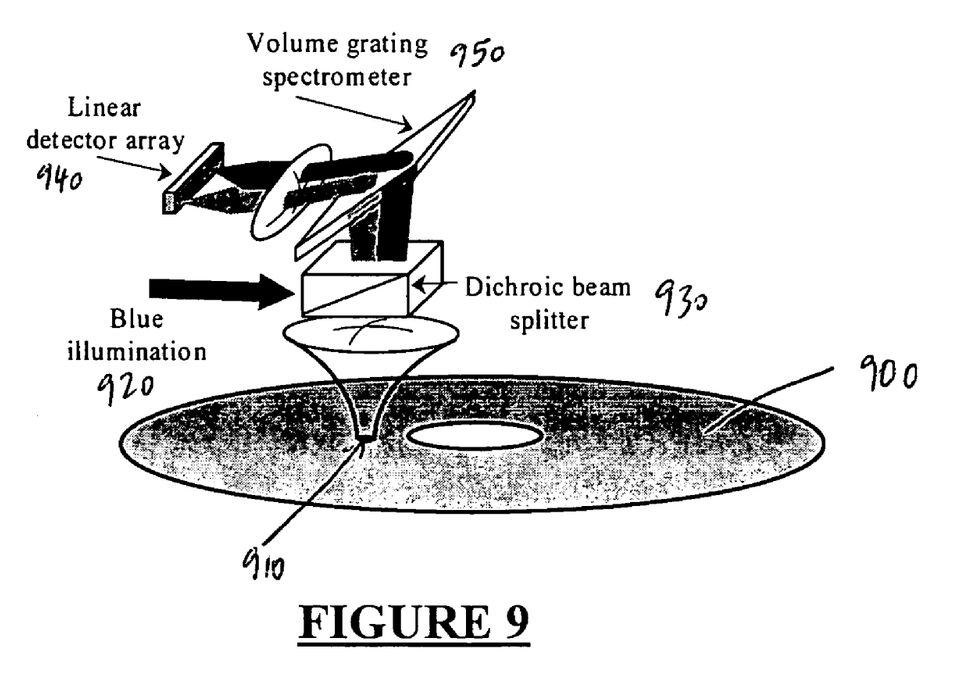
FIG. 9 illustrates a data storage system using optical disk and nano-tags with a volume grating-based detection system, according to one embodiment of the present invention.

According to one embodiment, optical tags are integrated in a DVD or CD with a volume grating-based detection system. The system is schematically illustrated in FIG. 9. Optical disk 900 with QDs 910 is illuminated by a focused blue illumination 920 emitted by a blue laser diode of the next generation DVD players having a 400 nm wavelength. The fluorescence is captured via a dichroic beam splitter 930 and collimated with a focusing lens in the linear detector array 940 and directed onto the volume grating spectrometer 950 that analyzes the spectral content.

Figure 10:
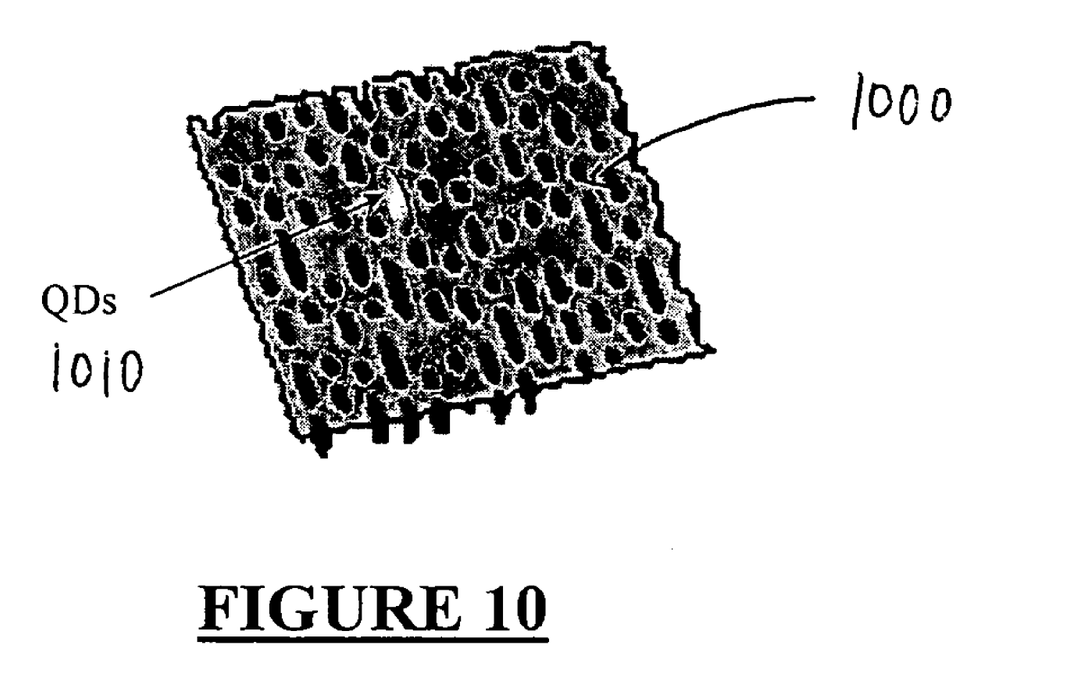
FIG. 10 illustrates an atomic force microscope image of the surface of a DVD disk with QDs deposited in its pits, according to one embodiment of the present invention.

The QDs are made up of an aqueous liquid obtained using a micro-fluidic device (both of these are explained above). In operation, the QDs are inserted in the pits of a commercial DVD or CD. The QDs are placed in the data layer of the DVD or CD by peeling aside the polymer layer. The placement of the QDs on the data layer is achieved using ink-jet nozzles. FIG. 10 illustrates an atomic force microscope image of the surface of a DVD disk 1000 with QDs 1010 deposited within the pits of the disk. By inserting the QDs in the pits of the DVD (or CD), the density of information is increased proportionally by the number of bits encoded in the spectral response of the fluorescent tag. The density of the QDs is calculated thus: Since the linewidth of each QD species is 20 nm at FWHM, it is possible to pack 50 spectral bands between 450 nm and 1500 nm. This spectral range matches that of commercially available silicon and GaAs detectors. By varying the amount of QDs of a particular color in the mixture, a gray level coding can be achieved. In experiments conducted by the inventors of this invention, 5 gray levels have been achieved with identification levels of 99.99%. Thus, the number of codes with 50 wavelengths and 6 gray levels is equal to $6^{50}$, which corresponds to $Log_2(6^{50})=129$ bits of information that can be packed in a single DVD spot. With a DVD cell size equal to 0.32 µm, the potential density of a single QD is 1260 bits/µm$^2$ or 0.8 Th/in$^2$. This high density is unparalleled by any of the existing technologies used for removable storage media, and provides a gain of fifty in information density compared with the next generation DVD technology. This large information density of the QD can be used to encode unique information.

Detection Device

Figure 11:
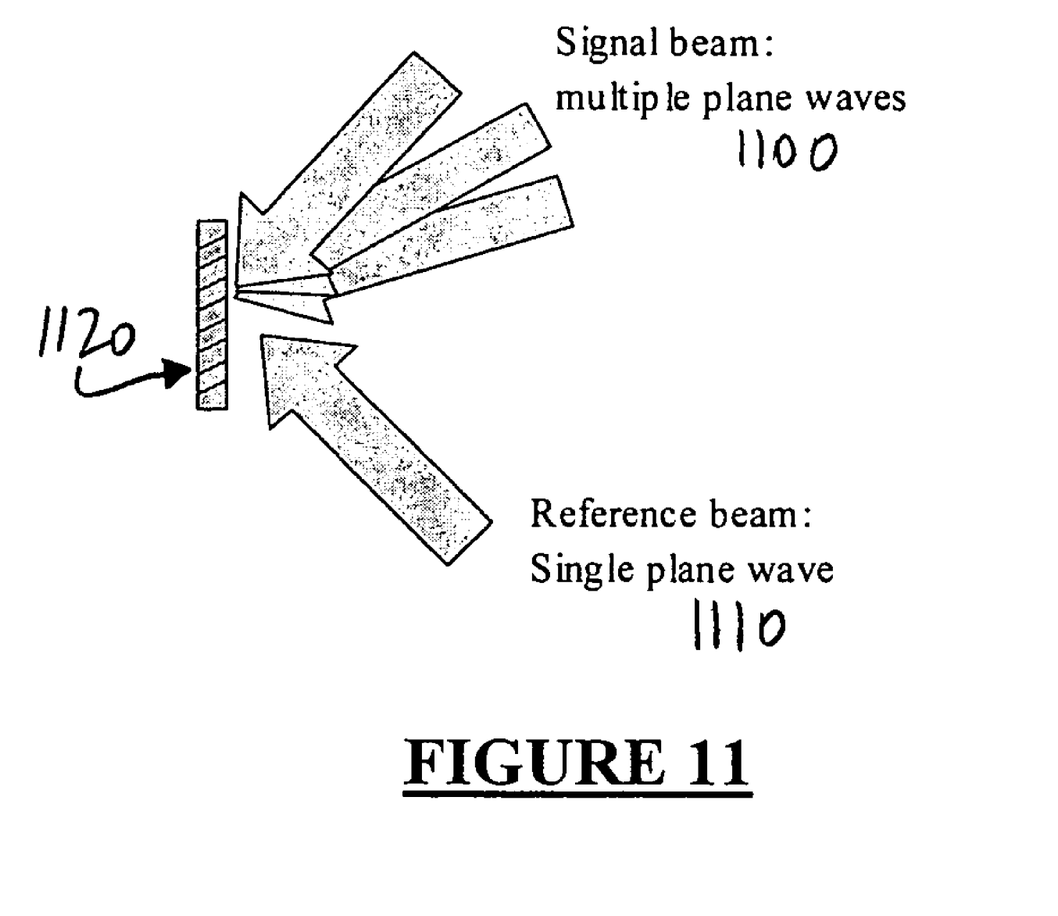
FIG. 11 illustrates the fabrication of a volume grating spectrometer, according to one embodiment of the present invention.

According to one embodiment, the detection device is based on a volume grating spectrometer. According to another embodiment, the fabrication of the grating is achieved by recording multiple filters with passbands centered on QD wavelengths. In operation, each filter is recorded by the interference of two plane waves, and by changing the angle of incidence of a signal beam, the center passband of the filter can be adjusted. FIG. 11 illustrates the fabrication of a volume grating spectrometer. 1100 is the signal beam having multiple plane waves and 1110 is the reference beam having a single plane wave. Both beams are incident on glass-based holographic medium 1120.

In operation, since the number of individual filters that can be superimposed with good efficiency depends on the available dynamic range of the holographic material's index variation ($\Delta n_0$), the multiplexing holograms using exposure schedules distribute the dynamic range equally among the N holograms as a sequential recording as follows:

$$\Delta n_N = \Delta n_0 / N \qquad (1)$$

However, if the N holograms are recorded simultaneously by generating N plane waves, the effective index modulation for each hologram becomes:

$$\Delta n_N = \Delta n_0 / \sqrt{N} \qquad (2)$$

Figure 12:
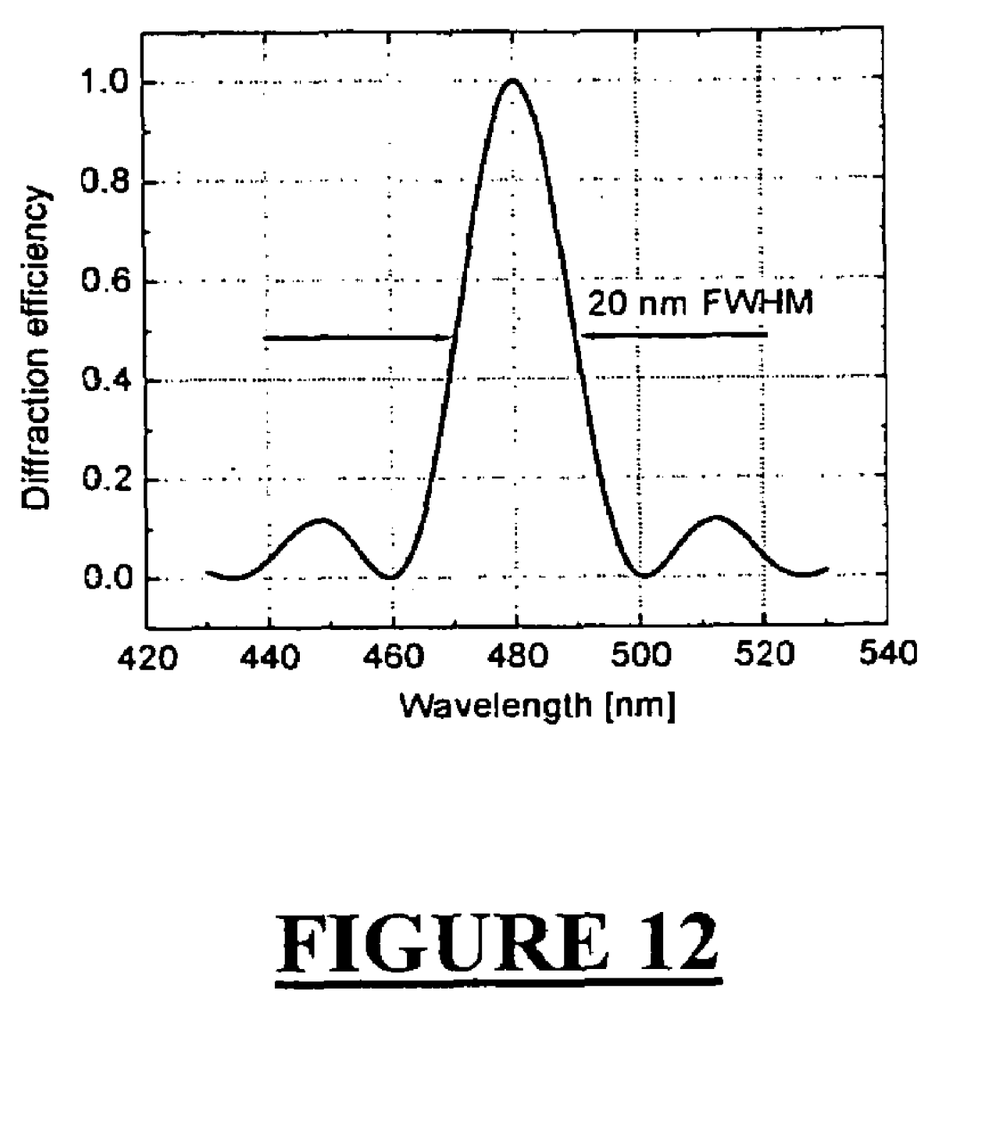
FIG. 12 illustrates a graph of the simulation of spectral response of a volume grating filter, according to one embodiment of the present invention.

FIG. 11 illustrates the recording geometry based on formula (2) above and can thus allow the multiplexing of $\sqrt{N}$ more holograms than the sequential recording illustrated by formula (1) above. In experiments conducted by the inventors of this invention, the glass holographic material is capable of developing a dynamic range of $\Delta n_0 = 1.5 \times 10^{-3}$. Thus a filter with bandwidth of 20 nm FWHM requires an index variation of $\Delta n = 2.2 \times 10^{-4}$ for a thickness of 3 mm. Using formula (2) above, the number of holograms that can be potentially stored with 100% efficiency at 20 nm bandwidth is 50. This bandwidth matches the linewidth of the QDs. FIG. 12 illustrates a graph of the simulation of spectral response of a volume grating filter having a thickness of 3 mm, 10 degrees between the diffraction and incident beams and having an index modulation of $\Delta n = 2.2 \times 10^{-4}$. Thus, the large gain obtained by simultaneous recording cannot be used in other holographic applications involving images because it is practically and physically not possible to generate all images simultaneously, however, the generation of multiple plane waves for the signal beam is ideal for the applications of the present invention.

Thus, a technology that combines fluorescent quantum dots and methods to dispense and detect them for a range of optical tagging applications is described in conjunction with one or more specific embodiments. The invention is defined by the following claims and their full scope and equivalents.

We claim:

1. A method of dispensing and detecting fluorescent quantum dots, comprising:
   dispensing said dots on a surface at a plurality of locations where each location includes quantum dots of a plurality of center wavelengths;
   exciting said dots with a UV light until said dots fluoresce; and
   analyzing said fluorescence with a spectrometer.

2. The method of claim 1 wherein said surface is a DVD disk.

3. the method of claim 1 wherein said surface is a CD disk.

4. The method of claim 1 wherein said surface further comprising an embossed material with a plurality of regions of pits and lands.

5. The method of claim 1 wherein dispensing said quantum dots further comprising:
   using an ink-jet nozzle to place said dots within a plurality of regions of pits of said surface.

6. The method of claim 1 wherein said spectrometer is a surface grating spectrometer.

7. The method of claim 1 wherein said spectrometer is a volume grating spectrometer.

8. The method of claim 7 wherein said volume grating spectrometer comprising a plurality of filters.

9. The method of claim 8 wherein said filters are immune to prolonged exposure to high temperature.

10. The method of claim 9 wherein said prolonged exposure is at least 2000 hours.

11. The method of claim 9 wherein said high temperature is at least 150° C.

12. The method of claim 9 wherein said plurality of filters is up to 41 filters.

13. The method of claim 1 wherein said dots are excited by a wavelength, wherein said wavelength is shorter than an emission peak of each of said dots.

14. A method of detecting a plurality of optical tags on an optical disk, comprising:
  integrating a plurality of optical tags on said optical disk;
  focusing a blue illumination from a blue laser diode of a DVD player to illuminate said tags;
  capturing a fluorescence emitted by said tags when illuminated;
  collimating said fluorescence; and
  analyzing a spectral content of said fluorescence.

15. A system to dispense and detect fluorescent quantum dots comprises:
  a dispenser to dispense said quantum dots on a surface at a plurality of locations where each location includes quantum dots of a plurality of center wavelengths;
  an exciter to excite said dots with a UV light until said dots fluoresce; and
  an analyzer to analyze said fluorescence.

16. The system of claim 15 wherein said surface is a DVD disk.

17. The system of claim 15 wherein said surface is a CD disk.

18. The system of claim 15 wherein said surface further comprises of an embossed material with a plurality of regions of pits and lands.

19. The system of claim 15 wherein said analyzer is a surface grating spectrometer.

20. The system of claim 15 wherein said analyzer is a volume grating spectrometer.

21. The system of claim 20 wherein said volume grating spectrometer comprises a plurality of filters.

22. The system of claim 21 wherein said plurality of filters is up to 41 filters.

23. The system of claim 21 wherein said filters are immune to prolonged exposure to high temperature.

24. The system of claim 23 wherein said prolonged exposure is at least 2000 hours.

25. The system of claim 23 wherein said high temperature is at least 150° C.

26. The system of claim 15 further comprises:
  a placement unit to place said dots within a plurality of regions of pits of said surface.

27. The system of claim 26 wherein said placement unit is an ink-jet nozzle.

28. The system of claim 15 wherein said dots are excited by a wavelength, wherein said wavelength is shorter than an emission peak of each of said dots.

29. A system for detecting a plurality of optical tags on an optical disk, comprises:
  an integrator to integrate a plurality of optical tags on said optical disk;
  a focuser to focus a blue illumination from a blue laser diode of a DVD player to illuminate said tags;
  a capturing unit to capture a fluorescence emitted by said tags when illuminated;
  a collimator to collimate said fluorescence; and
  an analyzer to analyze a spectral content of said fluorescence.

* * * * *